United States Patent [19]

Tamas et al.

[11] Patent Number: 5,646,135
[45] Date of Patent: Jul. 8, 1997

[54] METHOD FOR CONTROLLING COCCIDIOSIS

[75] Inventors: Tamas Tamas, East Brunswick; Dan A. Ostlind, Watchung, both of N.J.

[73] Assignee: Merck & Co., Inc., Rahway, N.J.

[21] Appl. No.: 614,450

[22] Filed: Mar. 12, 1996

Related U.S. Application Data

[63] Continuation of Ser. No. 324,556, Oct. 18, 1994, abandoned.

[51] Int. Cl.⁶ .................................................. A61K 31/65
[52] U.S. Cl. .................. 514/152; 514/256; 514/274; 514/289; 514/311; 514/460; 514/588; 514/601; 514/634; 514/647
[58] Field of Search ............................ 514/152, 256, 514/289, 274, 311, 460, 588, 601, 634, 647

[56] References Cited

U.S. PATENT DOCUMENTS

| | | | |
|---|---|---|---|
| 4,824,847 | 4/1989 | Raether | 514/256 |
| 4,855,299 | 8/1989 | Raether | 514/259 |

OTHER PUBLICATIONS

Siegmund, et al, The Merck Veterinary Manual, 5th, pp. 1128–1132 and 1569–1573 (1979).

*Primary Examiner*—Kevin E. Weddington
*Attorney, Agent, or Firm*—Mollie M. Yang; David L. Rose

[57] ABSTRACT

The present invention relates to an improved method for controlling coccidiosis in poultry which comprises administering to poultry on shuttle medication an additional medication prior to switching from the starter compound to the grower compound, and continuing the additional medication for a period after the switching.

6 Claims, No Drawings

METHOD FOR CONTROLLING COCCIDIOSIS

This is a continuation of application Ser. No. 08/324,556 filed on Oct. 18, 1994; now abandoned.

BACKGROUND OF THE INVENTION

Coccidiosis is a widespread poultry disease which is produced by infections with protozoans of the genus Eimeria which cause severe pathology in the intestines and ceca of poultry. Some of the most significant of these species are *E. tenella, E. acervulina, E. necatrix, E. brunetti* and *E. maxima*. This disease is generally spread by the birds picking up the organism at its infectious stage in droppings on contaminated litter or ground, or by way of food or drinking water. The disease is manifested by hemorrhage, accumulation of blood in the ceca, passage of blood in the droppings, weakness and digestive disturbances. The disease often terminates in the death of the animal, but the fowl which survive severe infections have had their market value substantially reduced as a result of the infection. Coccidiosis is, therefore, a disease of great economic importance and extensive work has been done to find new and improved methods for controlling and treating coccidial infections in poultry.

In the poultry industry it is common practice to include anticoccidial agents in poultry feed for most of the bird's life. Because the continuous administration of an anticoccidial agent promotes the likelihood of resistance to the agent, most poultry growers have adopted a so-called "shuttle program." In this medication strategy two or more anticoccidial agents are used sequentially during the broiler growout period. In a typical shuttle program the chickens are fed a first anticoccidial product (starter compound) for 21 days, and then switched to a ration containing a different anticoccidial product (grower compound). There may be a finisher product applied towards the end of the growout, and/or a 5–10 day drug withdrawal period. The principal objective of shuttle programs is to prevent or delay the emergence of drug-resistant coccidial strains that may be selected by continuous medication, as well as to control the disease itself.

The present inventors have found that the sequential use of anticoccidial agents leaves windows of compromised efficacy during or shortly after switching compounds, as manifested in increased lesions and oocyst shedding and decreased anticoccidial indices. This finding accords with industry observations that litter counts in commercial operations peak during the fourth week of the growout period, i.e. a week following the switch from starter to grower products in shuttle programs. Thus, even though the "shuttle" program may slow down resistance development, and/or the disease, it does not represent the optimal medication strategy in view of the gap of efficacy that may result from the switching of drugs.

SUMMARY OF THE INVENTION

The present invention provides an improved method for controlling coccidiosis in poultry which comprises administering, in sequence, to said poultry a first anticoccidial compound for two to four weeks, then switching to a second anticoccidial compound, wherein the improvement comprises: administering an additional anticoccidial medication up to 5 days prior to the switching and continuing said medication for up to 5 days after the switching.

DETAILED DESCRIPTION OF THE INVENTION

The present invention provides an improved method for the prevention and treatment of coccidiosis in poultry. The method comprises administering a first anticoccidial (a starter compound) for a period of from two to four weeks, and then switching to a second different anticoccidial (a grower compound); an additional anticoccidial medication (cross-over medication) is added to the regimen up to 5 days prior to the switching and is continued for up to 5 days after the switching. After the cessation of the grower compound, the poultry may be maintained on a drug-free diet, or they may be given a finisher compound, which is generally continued for one week.

In a preferred embodiment, the additional anticoccidial medication is administered for a total period of from 2 to 5 days; and more preferably, for a period of from 2 to 4 days.

Any agents that are effective in controlling coccidiosis in poultry may be utilized in the method of the present invention. Compounds suitable for use as starter compounds are for example nicarbazin, maxiban, robenidine, halofuginone and zoalene. Anticoccidial agents suitable for use as grower compounds are for example salinomycin, monensin, narasin and lasalocid. Anticoccidial agents suitable for use as finisher compounds are for example amprolium and clopidol.

The additional anticoccidial medication (the cross-over medication) may be a single, or a combination of two or more anticoccidial agents. Classes of anticoccidial agents suitable for use as cross-over medications are for example sulfonamides, tetracyclines, uracils, quinolines, and ionophores. Some specific compounds that can be mentioned as being suitable as cross-over medications are for example sulfaquinoxaline (SQ), amprolium, chlortetracycline (CTC), toltrazuril, lasalocid, amquinolate and ethopabate. Preferred cross-over medications are SQ in combination with amprolium (SQ+A), SQ in combination with CTC (SQ+CTC), SQ in combination with amquinolate, and toltrazuril and lasalocid administered as single agents.

The starter, grower and finisher compounds are most conveniently administered as a component of a feed composition. The anticoccidial compounds may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

The chickens are given the starter compound for the first two to four weeks, more preferably for about three weeks. At the end of the period, the first anticoccidial is stopped, and the chickens are switched to a second, different anticoccidial (grower compound), which is continued for one to three weeks, more preferably for about two weeks. After the grower compound, the chickens may be given a last anticoccidial (finisher compound) for a week, or they may be fed non-medicated diet.

The cross-over medication is preferably administered in drinking water, and is administered prior to switching from the starter to the grower compound. The medication is started from up to 5 days before the switch and continued for up to 5 days after the switch. Therefore, for a period of up to 10 days, the poultry receives the cross-over medication along with either the starter compound or the grower compound. More preferably, the cross-over medication is administered for a total period of from 2 to 5 days, and most preferably, for a total of about 3 days. The cross-over medication may be administered on a schedule of any combination of pre- and post-switching days. For example, the cross-over medication may be administered starting 24 hrs prior to switching and continuing for 48 hrs after the switch for a total of 3 days, or for 48 hrs prior and 96 hrs after switching for a total of 6 days, and the like.

The dosage ranges of the anticoccidial compounds (grower, starter, finisher, and the cross-over medication) used in the method of the present invention are those commonly known to be effective in controlling coccidiosis in poultry. For example, robenidine may be used as a starter compound at a concentration of from about 16 parts per million (ppm) to about 66 ppm, but usually at about 33 ppm; salinomycin may be used as a grower compound at a concentration of from about 60 ppm to about 100 ppm, but usually at about 60 to about 70 ppm; and amprolium may be used as a finisher compound at a concentration of from about 80 to about 250 ppm, but usually at about 100 to about 125 ppm. The range of suitable drug concentration and the preferred concentration for several specific agents and combination of agents used in cross-over medications are for example:

| Cross-Over Medication | Dose Range | Preferred Dose |
|---|---|---|
| amprolium | 60–300 | 250 |
| ethopabate | 4–40 | 40 |
| chlortetracycline (CTC) | 250–3000 | 2000 |
| sulfaquinoxaline (SQ) | 100–500 | 300 |
| toltrazuril | 2–20 | 10 |
| lasalocid | 80–150 | 125 |
| SQ + amprolium | 100–300 + 100–300 | 150 + 150 |
| SQ + CTC | 100–300 + 200–2000 | 150 + 500 |
| SQ + amquinolate | 100–300 + 30–100 | 150 + 60 |
| amprolium + ethopabate | 100–300 + 4–40 | 250 + 8 |

The actual quantity of the anticoccidial agent administered to the poultry in accordance with this invention will vary over a wide range and be adjusted to individual needs, depending upon species of the coccidia involved and the particular compound or combination of compounds used. The limiting criteria are that the minimum amount is sufficient to control coccidiosis and the maximum amount is such that the coccidiostat does not result in any undesirable effects.

The cross-over anticoccidial medication approach of the present invention provides improved protection for poultry against coccidiosis. The approach significantly decreases or eliminates the gap of compromised efficacy and reduces oocyst shedding during or shortly after the switching from starter to grower compound in "shuttle" medication. Lower oocyst shedding in the litter decreases the exposure of subsequent flocks to the infectious organisms, and would further retard the development of resistance.

The experiment described below is only illustrative of the method of the present invention, and is not to be construed as limiting the scope of the invention in any manner.

Experimental Design

One-week-old straight run male and female broiler chickens were obtained from Avian Services (Frenchtown, N.J.). These chickens were sorted by weight, and those in the middle of the distribution were grouped to provide a balanced pen weight throughout the experiment. Each pen housed five chickens. The chickens were divided into the following experimental groups: normal control, infected control, continuous medication, shuttle medication (switching from robenidine to salinomycin on day 0, 1, 2, 3, 4 or 5), or shuttle+crossover medication.

Chickens in all groups, except those in the normal control group, were infected with 100,000 E. tenella sporulated oocysts on day 0, and 200,000 E. acervulina sporulated oocysts on day 2. Robenidine, either as continuous medication or as part of a shuttle medication regimen, and salinomycin as continuous medication were included in the chicken feed at least one day prior to initial infection with E. tenella. (i.e. on day -1). Other continuous medications were started on day -1. In the continuous medication group, all chickens received their assigned drug for the entire duration of the experiment (i.e.. until day 7). In the shuttle medication group, all chickens started on robenidine, and groups of chickens were switched to salinomycin on day 0, 1, 2, 3, 4 or 5, and salinomycin was continued for the remainder of the experiment period. In the shuffle plus cross-over medication group, the shuttle treatment schedule was the same, and the cross-over medication was given 24 hours prior to switching and continued for 48 hours after switching for a total of 72 hours.

On day 7, chickens were euthanized in $CO_2$ gas, and weighed. The cecas were scored for E. tenella lesions and placed in 150 ml of 1% pepsin solution at pH 1 in 250 ml baffled flasks. The lower halves of the duodenal loops were then scored for mucosal E. acervulina lesions, and the upper halves were placed in 100 ml of pepsin. The cecas and the duodenal loops in pepsin were agitated at 30° C. and 200 RPM for 24 hours, and then the oocysts were counted by the conventional method (see e.g. Direction for use of Levy and Levy-Hausser Corpuscle-Counting Chamber. Hausser Scientific, Parsippany, N.J., 1973). The Merck Anticoccidial Index (A.C.I.) was also determined.

Drug Administration

Robenidine was mixed Purina Chicken Chow (Purina Ralston, St. Louis, Mo.) to achieve a concentration of 33 ppm. Similarly, salinomycin was mixed with the feed to achieve a concentration of 60 ppm.

All other compounds were administered in the water troughs at the specified concentrations (ppm): (a) amprolium+ethopabate (250+8); (b) sulfaquinoxaline (300); (c) chlortetracycline (2000); (d) lasalocid (150); (e) sulfaquinoxaline+amprolium (150+125); (f) sulfaquinoxaline+chlortetracycline (150+500); (g) sulfaquinoxaline+amquinolate (150+60); (h) toltrazuril (10); and lasalocid (125). Where a compound is not soluble in water, it is first dissolved in a small volume of ethanol, and the alcoholic solution is then diluted with water to the desired concentration. Each of the groups (a) to (h) was administered as continuous medication and as cross-over medication.

The anticoccidial agents used in the experiment are all known in the art, and are either commercially available or may be prepared according to literature procedures.

Results

Two separate experiments were carried out according to the experimental design and dosing schedule outlined above. In both experiments, each of the treatment group consisted of ten chickens (except in Experiment 1, the salinomycin continuous medication group included 20 chickens); the infected control groups consisted of either 20 (Experiment 1) or 40 chickens; and the normal control groups consisted of either 20 (Experiment 1 ) or 30 chickens. Lesions due to E. tenella and E. acervulina, oocysts of E. tenella and E. acervulina, as well as A.C.I. (see McManus et al, Development of Resistance to Quinoline Coccidiostats Under Field and Laboratory Conditions, J. Parasitol., 1968, 54:1190–1193) were determined using conventional methods, and the results are tabulated below as the average of each group with the standard error of means.

Lesion scores indicate the severity of the pathology caused by infection; scores range from 0 (no lesion) to 4 (severe infection). Oocyst production is expressed as percentage relative to untreated infected control group. A.C.I. is a measure of overall performance, and combines measurements on weight gain, survival rate, lesion score and oocyst production; a score of 180 or above is considered good, between 160 and 180 fair, and under 160 poor.

The abbreviations and their respective definitions appearing in the following Tables are: A.C.I.=anticoccidial index; E.a.=*Eimeria acervulina*; E.t.=*Eimeria tenella*; SQ=sulfaquinoxaline; A=amprolium; CTC= chlortetracycline; E=ethopabate; 808=amquinolate; R→S means switching from robenidine to salinomycin; and Days P.I. means the day post *E. tenella* infection on which the switching from robenidine to salinomycin occurred. The "control" group consisted of chickens that were infected but not treated.

lesions and oocyst shedding attributed to Eimeria infection. However, continuous medication is no longer a common practice in commercial poultry operations because it induces more rapid emergence of resistant strains of Eimeria species.

TABLE 1

Effect of Continuous Medication on Eimeria Lesions. Oocyst Shedding and Anticoccidial Index

| Treatment | Lesion Score | | Oocyst Production | | A.C.I. Score | |
|---|---|---|---|---|---|---|
| | E.a | E.t | E.a | E.t | E.a | E.t |
| *Experiment 1* | | | | | | |
| robenidine | 0 | 0.3 ± 0.1 | 0 | 0 | 192 ± 2 | 191 ± 2 |
| salinomycin | 1.2 ± 0.2 | 1.5 ± 0.3 | 34 ± 29 | 79 ± 25 | 173 ± 11 | 153 ± 11 |
| SQ + A | 0.2 | 0.7 ± 0.1 | 1 ± 1 | 0 | 188 ± 3 | 183 ± 4 |
| SQ + CTC | 0 | 0 | 0 | 0 | 188 ± 3 | 199 ± 5 |
| SQ + 808 | 0 | 0.6 ± 0.4 | 0 | 0 | 189 ± 2 | 183 ± 2 |
| toltrazuril | 0 | 0.2 ± 0.2 | 0 | 0 | 195 ± 2 | 193 ± 4 |
| lasalocid | 0 | 0.2 ± 0.2 | 0 | 0 | 179 ± 6 | 177 ± 4 |
| control | 2.9 ± 0.2 | 2.7 ± 0.2 | 100 | 100 | 105 ± 10 | 106 ± 10 |
| *Experiment 2* | | | | | | |
| robenidine | 0 | 0 | 0 | 0 | 193 ± 2 | 193 ± 2 |
| salinomycin | 1.8 ± 0.4 | 1.7 ± 0.1 | 11.5 ± 1.5 | 9.8 ± 1.8 | 173 ± 5 | 154 ± 3 |
| A + E | 0 | 0.1 ± 0.1 | 0 | 0 | 191 ± 1 | 190 |
| SQ | 0 | 0.05 ± 0.05 | 0 | 0 | 184 | 179 ± 5 |
| lasalocid | 0 | 0 | 0 | 0 | 163 ± 2 | 163 ± 2 |
| CTC | 0 | 0 | 0 | 0 | 179 ± 2 | 179 ± 2 |
| control | 2.8 ± 0.1 | 2.6 ± 0.1 | 100 ± 15 | 100 ± 15 | 102 ± 6 | 106 ± 7 |

The results in Table 1 show that all the anticoccidial agents tested as continuous medication were effective, or in the case of salinomycin, partially effective, in reducing the

TABLE 2

Eimeria Lesions with Shuttle and Shuttle + Cross-Over Medication

| Treatment | | 0 | 1 | 2 | 3 | 4 | 5 |
|---|---|---|---|---|---|---|---|
| | | | | Lesion Score | | | |
| *Experiment 1* | | | | | | | |
| R→S | E.a | 1.6 ± 0.1 | 1.4 ± 0.4 | 1.1 ± 0.3 | 0 | — | — |
| | E.t | 1.3 ± 0.1 | 2.1 ± 0.5 | 1.9 ± 0.2 | 0.90 | 0.3 ± 0.2 | 0.2 |
| R→S | E.a | 0.2 ± 0.2 | 0 | 0 | 0 | — | — |
| SQ + A | E.t | 1.5 ± 0.1 | 0.6 ± 0.1 | 0.3 ± 0.1 | 0.2 | 0.2 ± 0.2 | 0.2 |
| R→S | E.a | 0 | 0 | 0 | 0 | — | — |
| SQ + CTC | E.t | 1 ± 0.2 | 0.5 ± 0.2 | 0.6 | 0.2 ± 02 | 0 | 0 |
| R→S | E.a | 0 | 0 | 0 | 0 | — | — |
| SQ + 808 | E.t | 0 | 0.1 ± 0.1 | 0.7 ± 0.1 | 0.5 ± 0.1 | 0 | 0.1 ± 0.1 |
| R→S | E.a | 0 | 0 | 0 | 0 | — | — |
| Toltrazuril | E.t | 0.7 ± 0.3 | 0 | 0.1 ± 0.1 | 0.1 ± 0.1 | 0.2 ± 0.2 | 0 |
| R→S | E.a | 0 | 0 | 0 | 0 | — | — |
| Lasalocid | E.t | 0 | 0 | 0 | 0 | 0 | 0 |
| *Experiment 2* | | | | | | | |
| R→S | E.a | 1 | 1.2 ± 0.4 | 1 ± 0.2 | 0 | — | — |
| | E.t | 1.6 ± 0.4 | 1.3 ± 0.13 | 2 ± 0.2 | 1.9 ± 0.3 | 0.6 ± 0.2 | 0 |
| R→S | E.a | 1.2 ± 0.4 | 0.2 ± 0.2 | 0 | 0 | — | — |
| A+E | E.t | 1.1 ± 0.5 | 0.7 ± 0.1 | 0.2 | 0.1 ± 0.1 | 0 | 0 |
| R→S | E.a | 0 | 0 | 0 | 0 | — | — |
| SQ | E.t | 0.3 ± 0.3 | 0.4 ± 0.4 | 0.3 ± 0.1 | 0.1 ± 0.1 | 0 | 0 |
| R→S | E.a | 0 | 0 | 0 | 0 | — | — |
| Lasalocid | E.t | 0.2 | 0.1 ± 0.1 | 0 | 0 | 0 | 0 |
| R→S | E.a | 0.8 ± 0.2 | 0.3 ± 0.1 | 0 | 0 | — | — |
| CTC | E.t | 0.6 ± 0.2 | 0.1 ± 0.1 | 0 | 0 | 0 | 0 |

TABLE 3

Oocyst Counts with Shuttle and Shuttle + Cross-Over Medications

| Treatment | | Days P.I. | | | | | |
|---|---|---|---|---|---|---|---|
| | | 0 | 1 | 2 | 3 | 4 | 5 |
| | | | | Oocyst Production | | | |

*Experiment 1*

| Treatment | | 0 | 1 | 2 | 3 | 4 | 5 |
|---|---|---|---|---|---|---|---|
| R→S | E.a | 17 ± 8 | 58 ± 41 | 32 ± 2 | 0 | — | — |
|  | E.t | 39 ± 27 | 84 ± 57 | 104 ± 43 | 13 ± 11 | 0 | 0 |
| R→S | E.a | 0 | 0 | 0 | 0 | — | — |
| SQ + A | E.t | 19 ± 5 | 0.5 ± 0.5 | 0 | 0 | 0 | 0 |
| R→S | E.a | 0 | 0 | 0 | 0 | — | — |
| SQ + CTC | E.t | 12 ± 7 | 0.5 ± 0.5 | 0 | 0 | 0 | 0 |
| R→S | E.a | 0 | 0 | 0 | 0 | — | — |
| SQ + 808 | E.t | 0 | 0 | 8 + 7 | 0 | 0 | 0 |
| R→S | E.a | 0 | 0 | 0 | 0 | — | — |
| Toltrazuril | E.t | 3 ± 2 | 0 | 0 | 0 | 0 | 0 |
| R→S | E.a | 0 | 0 | 0 | 0 | — | — |
| Lasalocid | E.t | 0 | 0 | 0 | 0 | 0 | 0 |

*Experiment 2*

| Treatment | | 0 | 1 | 2 | 3 | 4 | 5 |
|---|---|---|---|---|---|---|---|
| R→S | E.a | 3 ± 3 | 31 ± 31 | 0 | 0 | — | — |
|  | E.t | 32.5 ± 7.5 | 70.5 ± 33.5 | 108.5 ± 48.5 | 0 | 1.5 ± 1.5 | 0 |
| R→S | E.a | 0 | 0 | 0 | 0 | — | — |
| A + E | E.t | 8 ± 6 | 0 | 0 | 0 | 0 | 0 |
| R→S | E.a | 0 | 0 | 0 | 0 | — | — |
| SQ | E.t | 1 ± 1 | 11.5 ± 11.5 | 0 | 0.5 ± 0.5 | 0 | 0 |
| R→S | E.a | 0 | 0 | 0 | 0 | — | — |
| Lasalocid | E.t | 0 | 0 | 0 | 0 | 0 | 0 |
| R→S | E.a | 0 | 0 | 0 | 0 | — | — |
| CTC | E.t | 0 | 0 | 0 | 0 | 0 | 0 |

TABLE 4

Anticoccidial Index with Shuttle and Shuttle + Cross-Over Medication

| Treatment | | Days P.I. | | | | | |
|---|---|---|---|---|---|---|---|
| | | 0 | 1 | 2 | 3 | 4 | 5 |
| | | | | A.C.I. Score | | | |

*Experiment 1*

| Treatment | | 0 | 1 | 2 | 3 | 4 | 5 |
|---|---|---|---|---|---|---|---|
| R→S | E.a | 166 ± 15 | 169 ± 12 | 173 ± 19 | 200 ± 1 | — | — |
|  | E.t | 170 ± 14 | 136 ± 30 | 137 ± 23 | 182 ± 7 | 193 ± 6 | 198 ± 1 |
| R→S | E.a | 197 ± 3 | 197 ± 2 | 196 ± 4 | 198 ± 2 | — | — |
| SQ + A | E.t | 172 ± 5 | 192 ± 2 | 196 ± 2 | 195 ± 2 | 194 ± 2 | 196 ± 2 |
| R→S | E.a | 198 ± 1 | 196 | 197 ± 7 | 191 ± 3 | — | — |
| SQ + CTC | E.t | 182 ± 1 | 190 ± 3 | 192 ± 1 | 195 ± 1 | 196 ± 8 | 191 ± 3 |
| R→S | E.a | 196 ± 3 | 197 ± 3 | 199 ± 2 | 194 ± 3 | — | — |
| SQ + 808 | E.t | 199 ± 4 | 195 ± 3 | 186 ± 1 | 192 ± 2 | 197 ± 2 | 198 ± 2 |
| R→S | E.a | 201 ± 3 | 198 ± 3 | 201 ± 2 | 197 ± 3 | — | — |
| Toltrazuril | E.t | 191 ± 1 | 198 ± 6 | 200 ± 4 | 197 ± 4 | 199 ± 1 | 197 ± 3 |
| R→S | E.a | 189 ± 1 | 197 | 199 ± 1 | 199 ± 4 | — | — |
| Lasalocid | E.t | 195 ± 2 | 190 ± 1 | 189 ± 1 | 187 | 194 ± 4 | 199 ± 4 |

*Experiment 2*

| Treatment | | 0 | 1 | 2 | 3 | 4 | 5 |
|---|---|---|---|---|---|---|---|
| R→S | E.a | 187 ± 2.5 | 167 ± 19 | 178 ± 8 | 202 ± 7.5 | — | — |
|  | E.t | 151 ± 24 | 156 ± 11 | 146 ± 13.5 | 173 ± 5.5 | 182 ± 8.5 | 202 ± 7.5 |
| R→S | E.a | 187 ± 1.5 | 201 ± 7.5 | 195 ± 0.5 | 186 ± 2.5 | — | — |
| A ± E | E.t | 188 ± 4.5 | 187 ± 0.5 | 197 ± 2.5 | 202 ± 4.5 | 195 ± 0.5 | 186 ± 2.5 |
| R→S | E.a | 203 ± 3.5 | 196 ± 2 | 198 | 194 ± 3.5 | — | — |
| SQ | E.t | 188 ± 7.5 | 184 ± 4 | 200 ± 4.5 | 195 ± 3.5 | 198 | 194 ± 3.5 |
| R→S | E.a | 188 ± 2 | 185 ± 4 | 185 ± 1 | 179 ± 1 | — | — |
| Lasalocid | E.t | 183 ± 4.5 | 185 ± 3 | 188 ± 2 | 185 ± 4 | 185 ± 1 | 179 ± 1 |
| R→S | E.a | 193 ± 5 | 190 ± 0.5 | 191 ± 1.5 | 188 ± 4 | — | — |
| CTC | E.t | 189 ± 1.5 | 183 ± 12 | 201 ± 3 | 193 ± 0.5 | 191 ± 1.5 | 188 ± 4 |

The data in Tables 2, 3 and 4 showed that the timing of the switch from robenidine to salinomycin affects the lesion and oocyst counts: switching during the middle stages of the Eimeria life cycle resulted in marginal or no activity. The addition of cross-over medication to the shuttle regimen provided full or significantly improved efficacy with decreased Eimeria lesions and increased anticoccidial indices. Most significantly, with cross-over medication, oocyst shedding was essentially eliminated. The low oocyst shedding achieved with cross-over medication would decrease the Eimeria exposure pressure in subsequent flocks housed in the same facility, and significantly retard the development of resistance.

What is claimed is:

1. An improved method for controlling coccidiosis in poultry which comprises administering, in sequence, to said poultry a first anticoccidial compound for two to four weeks, then switching to a second anticoccidial compound, wherein the improvement comprises: administering an additional anticoccidial medication up to 5 days prior to the switching and continuing said medication for up to 5 days after the switching.

2. The method of claim 1 wherein said additional anticoccidial medication is administered for a total period of from 2 days to 5 days.

3. The method of claim 1 wherein said additional anticoccidial medication is a member of a class selected from the group consisting of sulfonamides, tetracyclines, uracils, ionophores and quinolines.

4. The method of claim 1 wherein said additional anticoccidial medication is selected from the group consisting of: sulfaquinoxaline, amprolium, chlortetracycline, toltrazuril, lasalocid, amquinolate and ethopabate, and wherein said medication is administered for a total period of from 2 days to 5 days.

5. An improved method for controlling coccidiosis in poultry which comprises administering, in sequence, to said poultry a first anticoccidial compound for two to four weeks, then switching to a second anticoccidial compound, wherein the improvement comprises: administering an additional anticoccidial medication up to 5 days prior to the switching and continuing said medication for up to 5 days after the switching, wherein the first and second anticoccidial compound are administered via a medium that is different in kind from the medium for the additional anticoccidial medication.

6. The method of claim 5 wherein the first and second anticoccidial compound are administered via the feed stock, and the additional anticoccidial medication is administered via the drinking water.

\* \* \* \* \*